United States Patent [19]

Borden

[11] Patent Number: 5,157,678
[45] Date of Patent: Oct. 20, 1992

[54] LASER SAFE HOUSING FOR A PARTICLE MONITOR IN VACUUM PUMP LINES

[75] Inventor: Peter Borden, Palo Alto, Calif.

[73] Assignee: High Yield Technology, Sunnyvale, Calif.

[21] Appl. No.: 725,785

[22] Filed: Jul. 3, 1991

[51] Int. Cl.⁵ .............................................. H01S 3/04
[52] U.S. Cl. ........................................ 372/34; 372/43; 372/103
[58] Field of Search ...................... 372/34, 36, 39, 43, 372/103; 357/74

[56] References Cited

U.S. PATENT DOCUMENTS

| | | | |
|---|---|---|---|
| 4,179,194 | 12/1979 | Geller et al. | 372/34 |
| 4,834,491 | 5/1989 | Aoki et al. | 372/43 |
| 5,065,226 | 11/1991 | Kluitmans et al. | 372/43 |

*Primary Examiner*—Georgia Y. Epps
*Attorney, Agent, or Firm*—Skjerven, Morrill, MacPherson, Franklin & Friel

[57] ABSTRACT

A housing for a laser based particle monitor comprising a pair of pipes for directing particle flow through a chamber. In one embodiment, elbows are disposed on the piping such that the interior of the chamber cannot be viewed from a point outside the housing.

12 Claims, 4 Drawing Sheets

LASER SAFE HOUSING FOR A PARTICLE MONITOR IN VACUUM PUMP LINES

FIELD OF THE INVENTION

This invention relates to a housing for a laser product, and in particular to a housing for a laser-based particle monitor for vacuum applications.

DESCRIPTION OF THE RELATED ART

The U.S. Department of Health and Human Services, a branch of the Food and Drug Administration (FDA), issued safety regulations for laser products in HHS Publication FDA 86-8260, entitled "Compliance Guide for Laser Products," 1985 ("the FDA publication"). The FDA publication defines a laser product as "any device that constitutes, incorporates, or is intended to incorporate a laser or laser system."

In the FDA publication laser products are classified based upon the health hazard posed to persons operating the laser products. Laser product classes include, from least hazardous to most hazardous, Classes I, IIa, II, IIIa, IIIb and IV. The FDA publication describes Class I products as "devices that have emissions in the ultra violet, visible, and infrared sectra, and are limits below which biological hazards have not been established." Class IIIb products are "devices that emit in the ultraviolet, visible, and infrared spectra. Class IIIb products include laser systems ranging from 5 to 500 milliwatts in the visible spectrum. Class IIIb emission levels are ocular hazards for direct exposure throughout the range of the Class."

The FDA publication requires a protective housing for all laser Class I products. Further, "The protective housing must prevent human access to laser radiation in excess of the limits of Class I (and collateral radiation in excess of the collateral radiation limit) at all places and times where and when such human access is not necessary in order for the product to accomplish its intended function." (FDA publication, page 5). Thus, a Class IIIb laser can achieve a Class I ranking by being contained in a protective housing meeting the above description.

Laser products of particular importance in the present application are laser-based particle monitors for vacuum applications, and more particularly for laser-based particle monitors used in VLSI processing. Although the housing disclosed in this application is designed particularly for laser-based particle monitors, the housing can be used for any similar laser product incorporating a laser.

Laser-based particle monitors will now be discussed. Particle contamination from vacuum equipment in VLSI processing is estimated to be responsible for 40% of the total yield loss. As a consequence, it is important to control particle occurrence through use of standard techniques such as statistical process control. Statistical process control, in turn, requires sensitive real-time particle monitors that function reliably in the environment of the process equipment to report particle occurrence. Since statistics for particle occurrence become more reliable as more particles are counted, monitors are preferably designed to detect as many particles as possible. In addition, since the frequency of particle occurrence often increases with decreasing particle size, sensors are also preferably designed to detect the smallest particles possible. Laser-based particle monitors employ the principle that a particle passing through an intense laser beam will scatter light to a photodetector which then generates a measurable signal. Some laser-based particle monitors incorporate a laser of Class IIIb in order to provide a laser beam of sufficient intensity for particle detection.

FIGS. 1a and 1b illustrate a laser-based particle monitor of a type described in co-pending application Ser. No. 07/582,718, entitled "High Sensitivity, Large Detection Area Particle Sensor for Vacuum Applications", herein incorporated by reference. The monitor unit comprises a housing composed of a stainless steel or aluminum wall 1 enclosing a chamber 2. Within the chamber 2 is disposed the laser-based particle monitor. The laser-based particle monitor includes a wide laser beam 3, shown in end-view in FIG. 1a, which is directed along a longitudinal axis of the monitor. On either side of the laser beam 3 are photodetector mounts 4. A plurality of photodetectors (not shown) are disposed on photodetector mounts 4. Vacuum inlet pipe 5 and outlet pipe 5' are attached to the wall 1 and direct particle flow into and out of the chamber 2 through holes 6 and 6' defined by wall 1. Particle flow is created by a vacuum pump (not shown) connected to outlet pipe 5'. Particles drawn into the chamber 2 through the inlet pipe 5 pass between and around the photodetector mounts 4 and into the outlet pipe 5'. A portion of the particles drawn into the chamber 2 pass through the laser beam 3 causing scattered light which is detected by the plurality of photodetectors disposed on photodetector mounts 4. The number of detections is then processed to determine the total number of particles passing through the chamber 2.

The broken line S in FIG. 1b denotes a line-of-sight into the chamber 2 through one of the holes 6 and 6'. When installed in vacuum lines used for VLSI processing, the possibility exists that the opening of vents or valves can result in an equipment operator viewing the laser beam 3 along line-of-sight S through the opening 6 in the chamber 2. Because the lasers used in some laser-based particle monitors are of Class IIIb or higher, this possibility must be prevented by the particle monitor manufacturer in order to meet the safety regulations of the FDA discussed above.

FIG. 2 illustrates a prior art method for housing a laser-based particle monitor in order to fulfill the safety requirements of the FDA publication. The inlet pipe 5 leading to the chamber 2 through opening 6 includes a series of chevron shaped baffles 20 which prevent direct viewing into the chamber 2 along line-of-sight S. However, the chevron shaped baffles 20 restrict the flow of gas through the pipe and create turbulence. This causes a decrease in the accuracy of the sensor due to "impaction"; that is, the loss of particles which strike and adhere to the surface of the baffles 20. In addition, production of the baffles is expensive.

SUMMARY

A housing for laser products according to the present invention comprises at least one wall surrounding a chamber, the wall defining at least one hole, and at least one opaque hollow member having a first end connected to the wall around the hole. The opaque hollow member also has a second end, and one bend such that direct viewing of the chamber from the second end is impeded by a portion of the opaque hollow member.

According to a first embodiment of the present invention, the opaque hollow member comprises a pipe having a first section connected to the wall, an elbow connected to the first section, and a second section connected to the elbow such that the elbow is disposed between the first and second sections. The length of the first and second sections are long enough such that the chamber cannot be viewed from an open-end of the second section.

A housing of a second embodiment of the present invention comprises first, second and third sections, and first and second elbows disposed between said first and second sections, and said second and third sections, respectively. The first, second and third sections are made long enough such that the chamber cannot be viewed from an open-end of the third section.

An advantage of the present invention is that the present housing does not affect particle flow as occurs in the prior art baffled housing. A further advantage is that the present housing provides a simple structure for meeting the FDA safety requirements. A further advantage is that production of the present housing is less expensive than production of the baffled housing taught in the prior art.

BRIEF DESCRIPTION OF THE DRAWINGS

FIG. 1b is a side sectional view of a prior art laser based particle monitor taken along line A—A of FIG. 1a.

DETAILED DESCRIPTION OF THE PREFERRED EMBODIMENTS

Figure 1A:
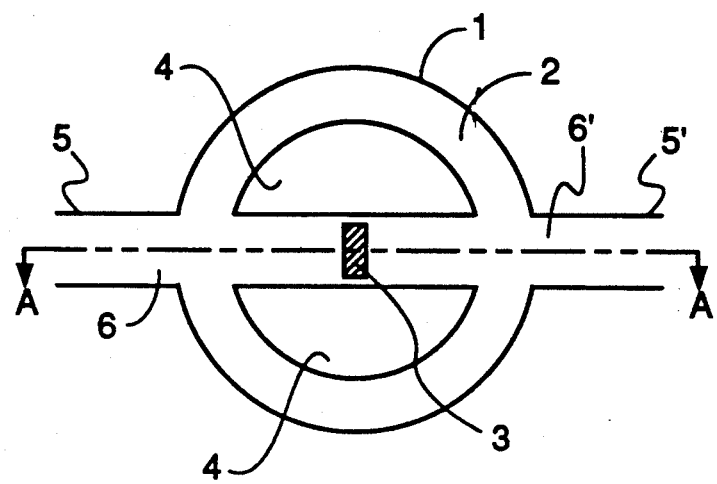
FIGS. 1a is a top sectional view of a prior art laser based particle monitor.
Figure 1B:
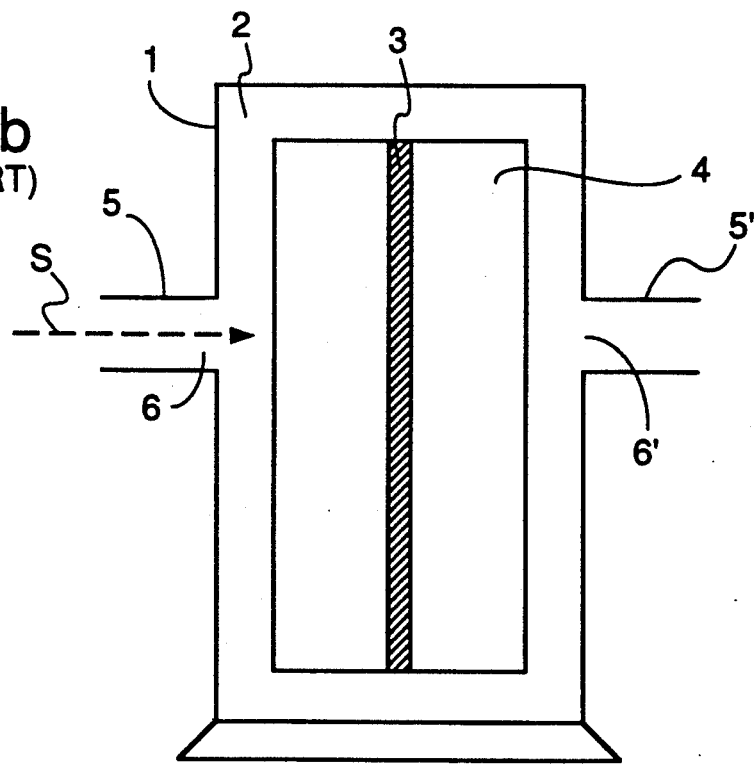
Figure 2:
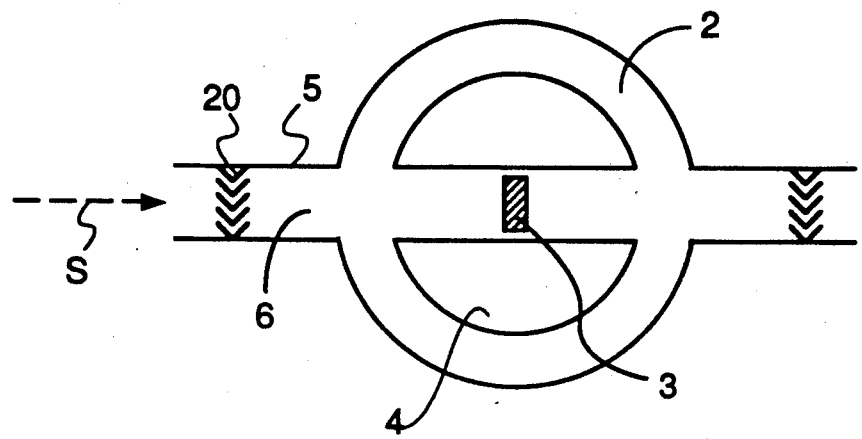
FIG. 2 is a top view showing a prior art housing for a laser based particle monitor.
Figure 4:
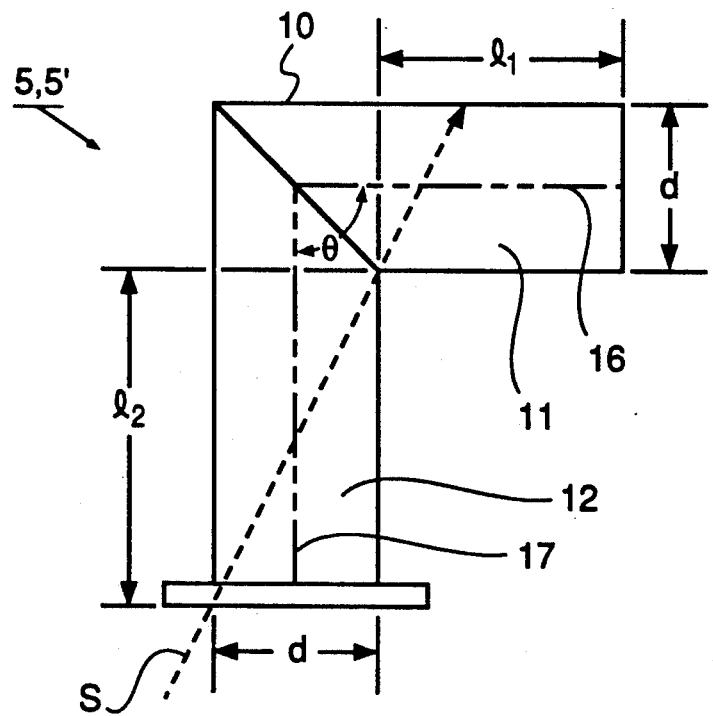
FIG. 4 is a top view of a pipe of the first embodiment.
Figure 5:
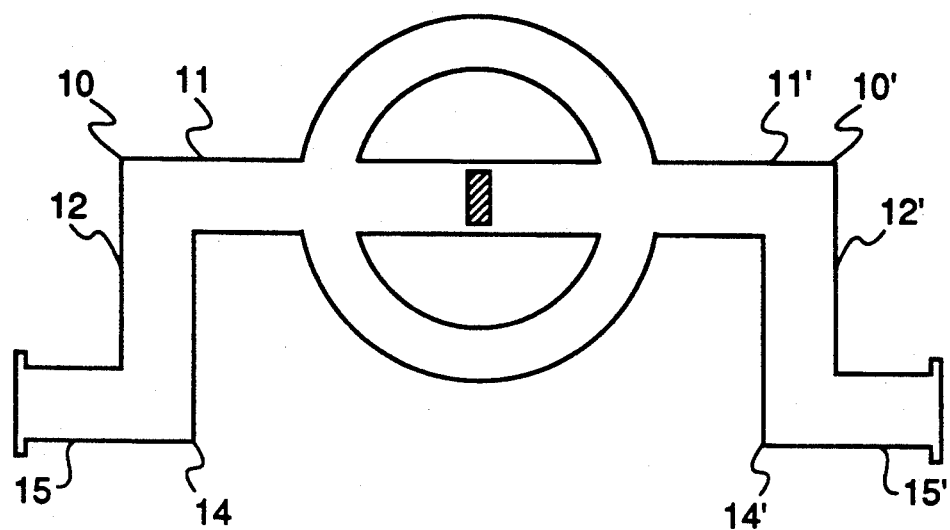
FIG. 5 is a top view of a second embodiment of the present invention.
Figure 6:
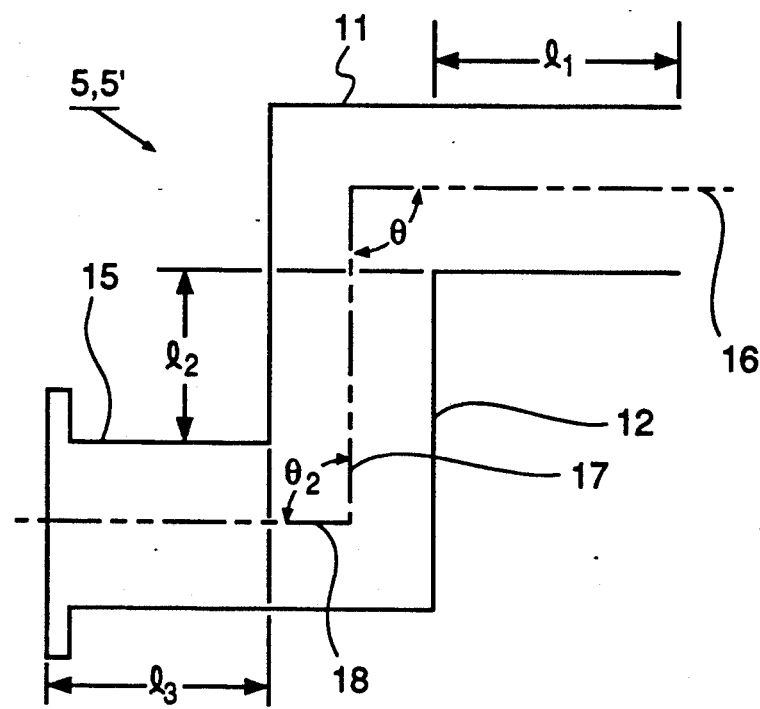
FIG. 6 is a top view of a pipe of the second embodiment.

A housing for laser products in accordance with the present invention is shown in FIGS. 3–6. A first embodiment of the present invention is shown in FIGS. 3a, 3b and 4. A second embodiment of the present invention is shown in FIGS. 5 and 6.

Figure 3A:
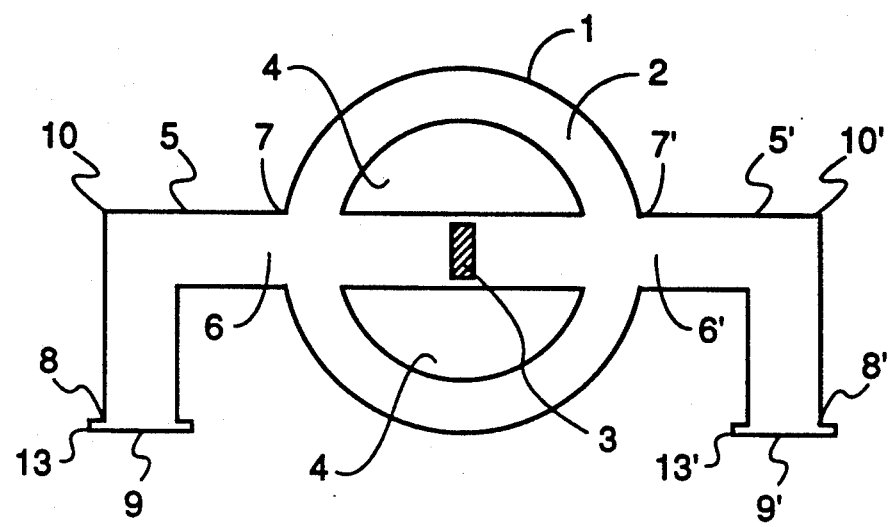
FIGS. 3a and 3b are top and side views of first embodiment of a housing of the present invention.
Figure 3B:
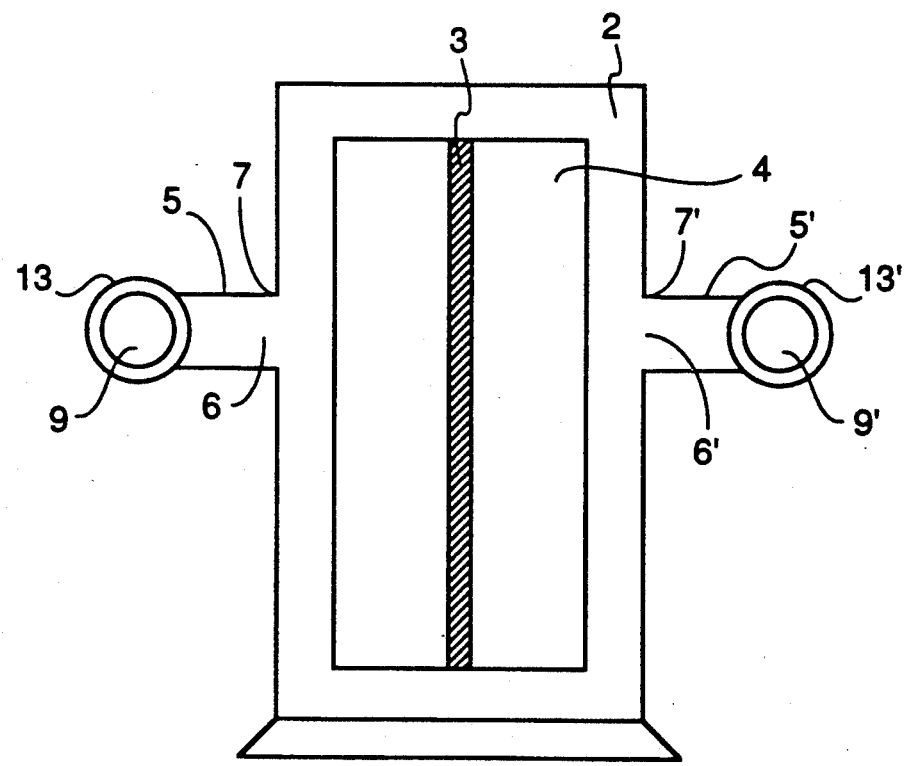

Referring to FIGS. 3a and 3b, the housing includes an outer wall 1 surrounding a chamber 2 within which is disposed a laser-based particle monitor which emits a laser beam 3. The outer wall also defines a pair of holes 6 and 6'. Inlet pipe 5 and outlet pipe 5' are respectively connected at the first ends 7 and 7' to an outer surface of the outer wall 1 around the hole 6 and 6' such that particles traveling along inlet pipe 5 pass into chamber 2 through hole 6 and pass out of chamber 2 through hole 6' into outlet pipe 5'. The housing comprises bends or elbows 10 and 10' respectively located on pipes 5 and 5' such that a laser beam 3 disposed in chamber 2 cannot be viewed by looking through either pipe 5 or 5' from either opening 9 or 9'. The second ends 8 and 8' respectively include openings 9 and 9' and flanges 13 and 13' for connecting the housing to vacuum equipment.

FIG. 4 illustrates in greater detail one of the pipes 5 and 5' of the first embodiment. As indicated, first section 11 has a length $l_1$ extending from first end 7 to an interior corner of elbow 10. Likewise, second section 12 has a length $l_2$ extending from second end 8 to the interior corner of elbow 10. First section 11 and second section 12 define first longitudinal axis 16 and second longitudinal axis 17, respectively, extending in a direction parallel to first length $l_1$ and second length $l_2$. Elbow 10 is disposed between first section 11 and second section 12. Elbow 10 is characterized by an angle $\theta$ which is formed by the intersection of the first longitudinal axis 16 and the second longitudinal axis 17. The cross-section of first section 11, second section 12 and elbow 10 is preferably substantially the same to facilitate assembly. As indicated in FIG. 4, each section has a circular cross-section having an interior diameter d. However, any cross-sectional shape may be used.

Elbow 10 may be formed using portions of first section 11 and second section 12 by mitre cutting the sections at an angle and connecting the angled ends to form an elbow. Elbow 10 may also be a separate piece connected to flat cut ends of first section 11 and second section 12. The angle $\theta$ of the elbow 10 may be virtually any angle, as long as the combination of angle $\theta$ and the lengths $l_1$ and $l_2$ prevent direct viewing of chamber 2. The elbow 10 may be a sharp 90° corner, as shown in FIG. 4, or may be curved to provide a smoother gas flow.

The lengths $l_1$ and $l_2$ of the first section 11 and second section 12, respectively, may be determined using simple geometry by drawing the pipe 5 as shown in FIG. 4 and using a straight edge to determine the lengths $l_1$ and $l_2$ at which the chamber 2 cannot be viewed from the second end opening 9. In other words, if a line-of-sight S from the second end opening 9 through the interior portion of pipe 5 to the chamber 2 intersects a portion of an inner surface of pipe 5, then the laser beam 3 cannot be directly viewed from a point outside the housing.

By proper selection of the lengths of the straight sections of the pipes 5 and 5' viewing of the laser beam 3 through the openings 7 and 7' can be prevented during operation of the laser-based particle monitor. This design meets the safety regulations set forth in the FDA publication because the laser beam cannot be viewed from the second end openings 9 and 9'.

The housing of the present invention has several advantages over the prior art baffled housing. First, the present housing does not affect particle flow to the extent occurring in the prior art baffled housing. A. Roth teaches in *Vacuum Technology*, 2nd, revised edition, North-Holland Publishing Co., 1976, 1982, that the conductance around a 90° elbow (a "trap") is greater than the conductance through a series of baffles, as taught in the prior art. In addition, the number of particles passing around the bend of the elbow is substantially higher than the number of particles passing through the baffles system of the prior art due to the tendency of the particles to impinge upon the baffles. Second, the housing provides a simple structure for meeting the FDA safety requirements. Third, production of the housing of the present invention is less expensive than production of the baffled housing taught in the prior art.

The housing of the present invention can be used not only in laser-based particle monitors, but in many other laser product applications. In addition, the housing may be modified by replacing either the inlet pipe 5 or the outlet pipe 5' with opaque vacuum or other equipment which prevents direct viewing of the chamber 2.

FIG. 5 illustrates a second embodiment of the present invention. The second embodiment includes third sections 15 and 15' and second elbows 14 and 14'. This embodiment provides the advantage of installation in linearly arranged vacuum lines.

FIG. 6 illustrates in greater detail one of the pipes 5 or 5' of the second embodiment. The third section 15 has the same cross section as first section 11 and second section 12. The third section has a length $l_3$ and a longitudinal axis 18. Second elbow 14 has an angle $\theta$ defined by the intersection of longitudinal axes 17 and 18. In determining the lengths of the three sections 11, 12 and 15, the drawing method taught in the description of the first embodiment, above, may be used.

In practice, it is preferred to minimize the distance between the flanged faces to facilitate installation in vacuum lines; therefore, it is preferable to minimize $l_1$ and $l_3$.

The detailed description above is intended to illustrate the specific embodiments of the present invention and is intended not to be taken in a limiting sense. Numerous modifications and variations may be made to the housing described in the first and second embodiments within the scope of the present invention. For example, the inlet pipe 5 or outlet pipe 5' may be replaced with opaque equipment which prevents viewing of the chamber 2.

The present invention is defined by the following claims.

What is claimed is:

1. A housing for a laser product comprising:
   a wall surrounding a chamber, said wall defining a hole; and
   an opaque hollow member having first and second ends, said first end connected to said wall around said hole;
   said opaque hollow member having a bend such that direct viewing of said chamber from said second end is impeded by said opaque hollow member.

2. A housing of claim 1 wherein said opaque hollow member comprises two straight cylindrical portions, and said bend comprises an elbow portion, said elbow being disposed between said two straight cylindrical portions.

3. A housing of claim 2 wherein said two straight cylindrical portions comprise first and second cylindrical portions and said elbow portion comprises a first elbow portion, said first and second cylindrical portions having a substantially common interior diameter d.

4. A housing of claim 2 wherein said two straight cylindrical portions comprise first, second and third cylindrical portions and said elbow portion comprises first and second elbow portions, said first elbow portion disposed between said first and second cylindrical portions and said second elbow portion disposed between said second and third cylindrical portions, said first, second and third cylindrical portions having a substantially common interior diameter d.

5. A housing of claim 1 wherein said laser product is a laser-based particle monitor.

6. A housing of claim 1 wherein said housing is connected to a vacuum producing device.

7. A method for housing a laser product comprising:
   surrounding a chamber with a wall defining a hole; and
   connecting an opaque hollow member having first and second ends to said wall around said hole, said opaque hollow member having a bend such that direct viewing of said chamber from said second end is impeded by said opaque hollow member.

8. A method for housing of claim 7 wherein said opaque hollow member comprises two straight cylindrical portions, and said bend comprises an elbow portion, said elbow being disposed between said two straight cylindrical portions.

9. A method for housing of claim 8 wherein said two straight cylindrical portions comprise first and second cylindrical portions and said elbow portion comprises a first elbow portion, said first and second cylindrical portions having a substantially common interior diameter d.

10. A method for housing of claim 8 wherein said two straight cylindrical portions comprise first, second and third cylindrical portions and said elbow portion comprises first and second elbow portions, said first elbow portion disposed between said first and second cylindrical portions and said second elbow portion disposed between said second and third cylindrical portions, said first, second and third cylindrical portions having a substantially common interior diameter d.

11. A method for housing of claim 7 wherein said laser product is a laser-based particle monitor.

12. A method for housing of claim 7 further comprising connecting said housing to a vacuum producing device.

* * * * *